United States Patent
Dugot

[11] Patent Number: 5,738,521
[45] Date of Patent: Apr. 14, 1998

[54] METHOD FOR ACCELERATING OSSEOINTEGRATION OF METAL BONE IMPLANTS USING ELECTRICAL STIMULATION

[75] Inventor: Richard S. Dugot, New York, N.Y.

[73] Assignee: Biolectron, Inc., Hackensack, N.J.

[21] Appl. No.: 684,379

[22] Filed: Jul. 19, 1996

[51] Int. Cl.⁶ .................................................. A61C 8/00
[52] U.S. Cl. ........................ 433/173; 433/174; 600/14; 607/51
[58] Field of Search .................... 433/173, 174; 600/13, 14; 607/51, 52

[56] References Cited

U.S. PATENT DOCUMENTS

| | | |
|---|---|---|
| 3,918,440 | 11/1975 | Kraus . |
| 4,027,392 | 6/1977 | Sawyer et al. . |
| 4,175,565 | 11/1979 | Chiarenza et al. . |
| 4,459,988 | 7/1984 | Dugot . |
| 4,535,775 | 8/1985 | Brighton et al. . |
| 4,558,701 | 12/1985 | Spalten . |
| 4,600,010 | 7/1986 | Dugot . |
| 4,781,591 | 11/1988 | Allen . |
| 4,960,381 | 10/1990 | Niznick . |
| 5,383,935 | 1/1995 | Shirkhanzadeh . |

*Primary Examiner*—Paul B. Prebilic
*Attorney, Agent, or Firm*—Baker & Botts, L.L.P.

[57] ABSTRACT

A method and apparatus for accelerating osseointegration of titanium implants in bone to anchor a prosthetic or dental device thereon in which an alternating electric signal of symmetrical wave form and of substantially constant amplitude having a frequency in the range of from about 40 to 100 KHz and providing a constant current in the range of from about 10 to 100 microamperes is supplied to at least one electrode in contact with the metal implant and another electrode in contact with the skin in proximity to the implant.

11 Claims, 2 Drawing Sheets

METHOD FOR ACCELERATING OSSEOINTEGRATION OF METAL BONE IMPLANTS USING ELECTRICAL STIMULATION

BACKGROUND OF THE INVENTION

This invention relates to a method and apparatus for the application of electrostimulation to the area of a metal implant to increase the rate of osseointegration of the metal implant in bone, thus increasing the speed and efficacy of healing.

In recent years, the response of living tissues and cells to various forms of electrical stimulation has been extensively investigated. Out of this work have evolved proposals for promoting the healing of bone fractures.

Within the last decade metal implants have revolutionized the field of prosthetic dentistry and orthopaedic surgery. The basic principle of implants is that a physiologically compatible metal, such as titanium, can be surgically inserted into a human bone, thus providing the foundation upon which a prosthetic device can be mounted or fabricated. The term "osseointegration" describes the process of bone growth at the interface between the metal implant and the bone.

Implant therapy now plays an integral role in the field of prosthetic dentistry for anchoring dentures. It is the only mode of therapy for many patients, and it has the advantage of providing a technique for mounting dentures which have a far longer life than traditional dentures, bridges and crowns. At present dental implant therapy faces major drawbacks, namely, major cost and patient discomfort caused by lengthy surgical procedures and the slow process of osseointegration.

There have been many efforts to increase the rate of osseointegration of metallic dental implants in the jawbone by self-contained current generating devices for promoting bone growth about the dental implant. Such devices are disclosed in U.S. Pat. Nos. 4,027,392, 4,558,701, 4,781,591 and 5,383,935.

U.S. Pat. No. 4,175,565 discloses a method and apparatus for stimulating osseogenic activity in a jawbone to anchor a dental implant by applying a direct current to said implant acting as a cathode and a second electrode acting as an anode placed on the skin of the subject, preferably on the earlobe. It is suggested therein that bone formation is enhanced in the area of the electrode acting as a cathode and that bone material deteriorates adjacent the area of the electrode acting as the anode and that the application of alternating current would not produce optimum results.

SUMMARY OF THE INVENTION

The invention relates generally to a method and apparatus for accelerating osseointegration of metallic bone implants, and more particularly in a jawbone to anchor a dental implant, for providing the foundation upon which a prosthetic device can be fabricated or mounted. The acceleration is accomplished by supplying an alternating electric signal of symmetrical wave form and of substantially constant amplitude to at least one electrode in contact with the metal implant and to at least one other electrode in contact with the skin. The alternating electric signal has a frequency in the range of from about 40 to 100 KHz at a constant effective current in the range of from 10 to 100 microamperes rms for a period of time sufficient to complete osseointegration to a point where the implant can be used for fabricating or mounting a prosthesis or denture.

In the case of an osseointegration of a metal implant in a jawbone, one of the electrodes can be mounted directly to the implant by suitable means, such as a metal screw, which can be anchored by the patient, and the other electrode can be either anchored to the jawbone in proximity to the implant or left floating in the mouth of the patient. In this way the patient can administer the electrical stimulation at his convenience at home without the necessity for treatment under the supervision of a physician or dentist. The term "skin" is used herein to include the gum tissue within the mouth.

PREFERRED EMBODIMENTS OF THE INVENTION

The invention will be described below in its preferred embodiment for stimulating bone growth for anchoring dental implants, although it should be understood that the method and apparatus is suitable for use in anchoring metal implants in bone in other parts of the body.

According to the invention, a conventional metal implant 10, such as titanium, is inserted into the jawbone 11 in a conventional manner. Titanium implants are well tolerated by biological tissues, including bone, and are currently used in prosthetic dentistry, orthopaedic surgery and craniomaxillofacial reconstruction. Once the bone is inserted, bone develops directly on the surface of the implant. A titanium implant generally requires two surgical procedures, the first for placement of the titanium implant and the second for mounting of the prosthesis or denture to the implant. There is usually a five to eight month healing period between the surgeries.

To accelerate the osseointegration process, an electrical current is applied to the implant immediately following insertion into the bone. This procedure not only affords greater comfort to the patient but also reduces the costs and time necessary for completing the mounting of the prosthetic or dental device.

Figure 1:
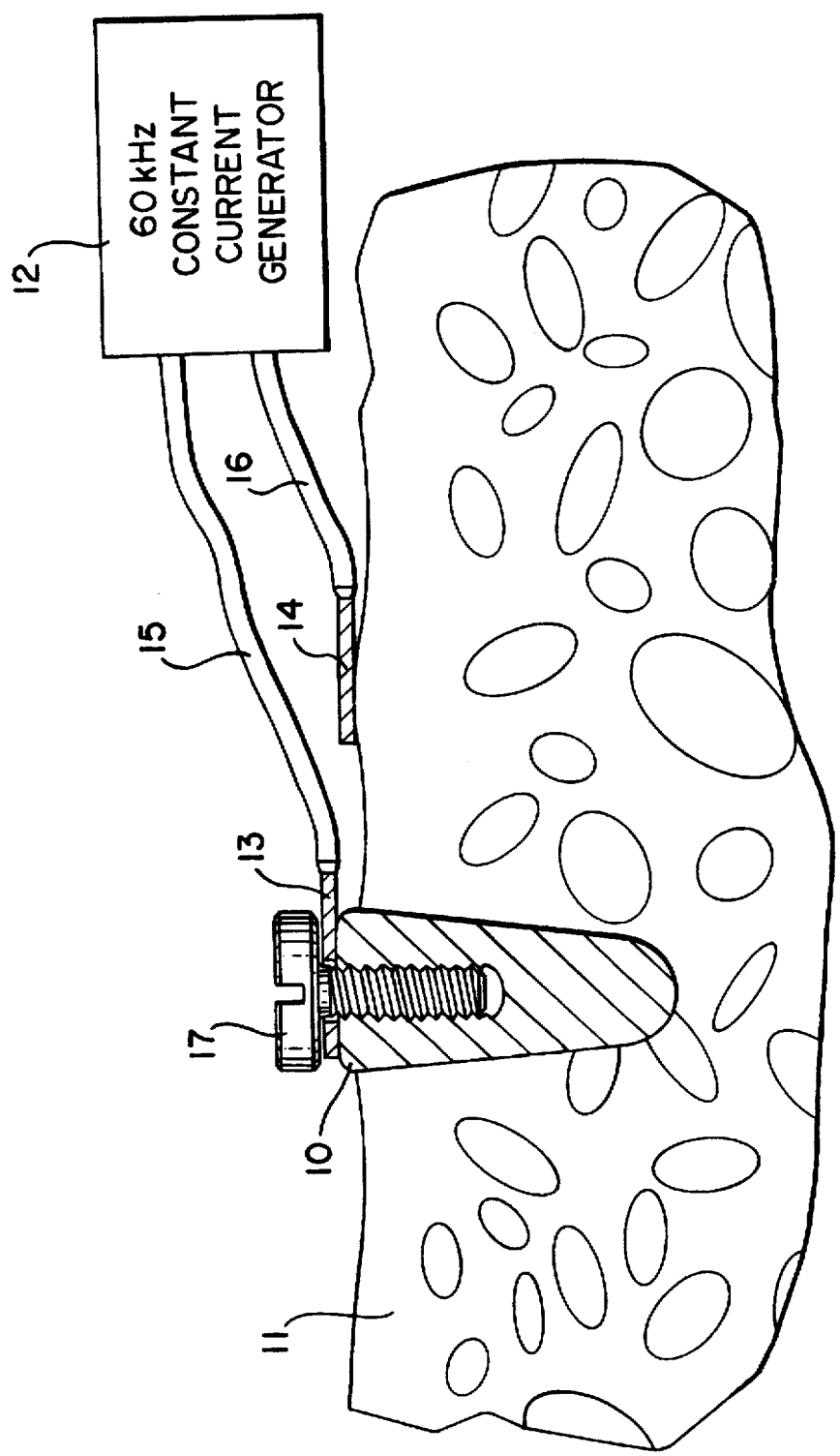
FIG. 1 is a schematic showing a method and apparatus for stimulating bone growth for anchoring a dental implant.
Figure 2:
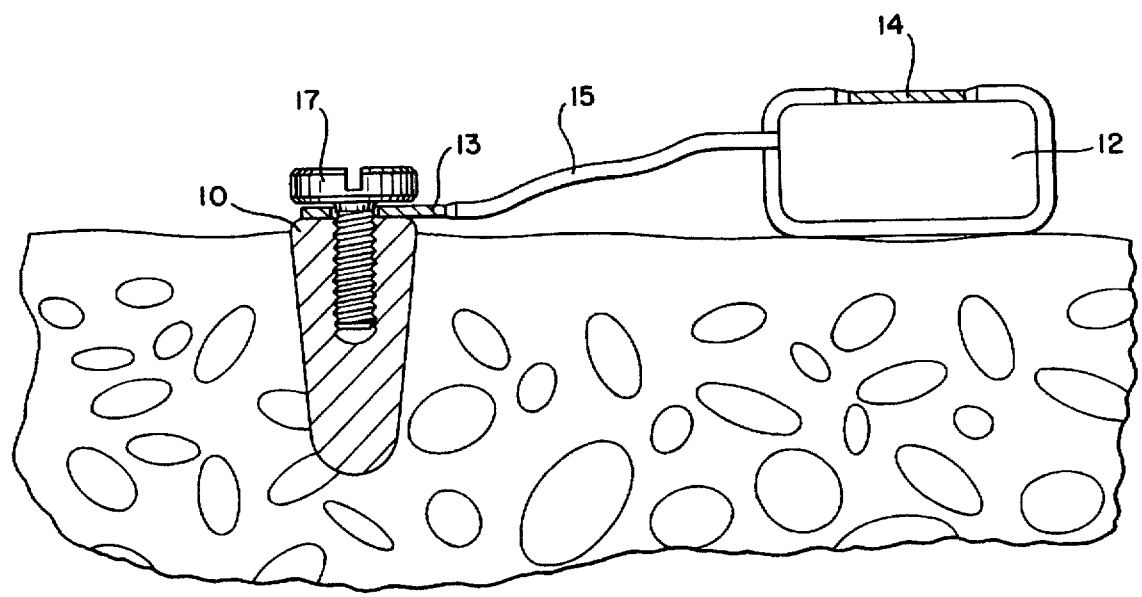
FIG. 2 is a schematic of the apparatus shown in FIG. 1 in which the generator housing serves as one of the electrodes.
Figure 3:
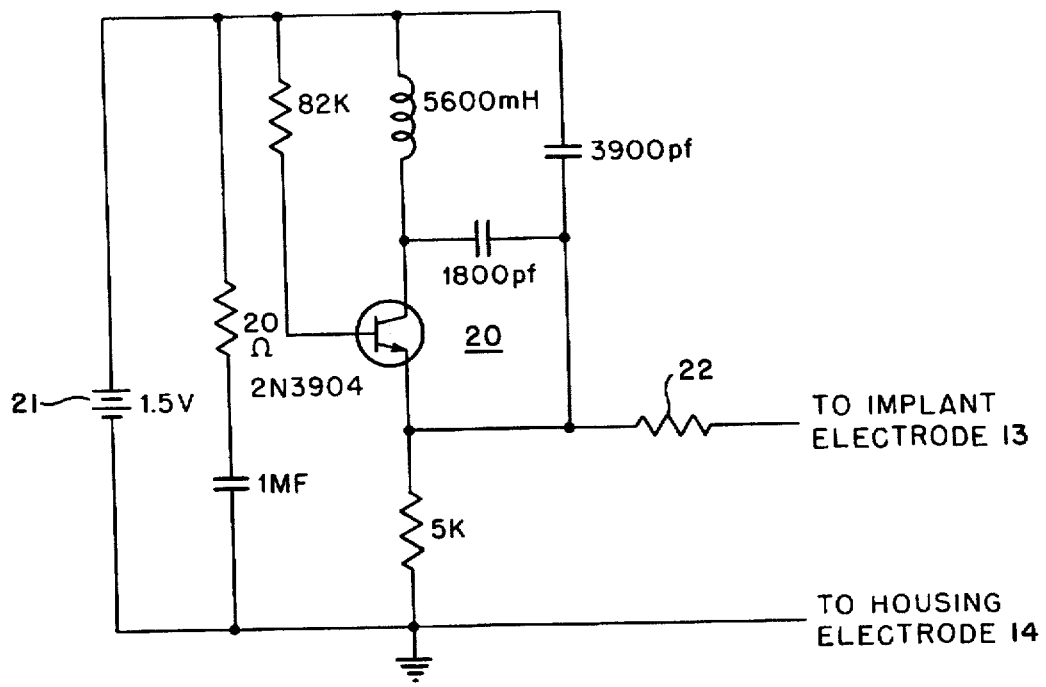
FIG. 3 is an oscillator circuit for use in connection with method and apparatus of the present invention.

The electrical bone growth stimulation is provided by a constant current generator 12, described in the Dugot U.S. Pat. No. 4,459,988 and U.S. Pat. No. 4,600,010. This generator, powered by a 9 volt battery, is useful for accelerating osseointegration of metal bone implants to anchor them in bone in parts of the body outside the mouth, such as the legs or hips. The generator accelerating osseointegration for dentures is preferably a miniature version of that generator which is capable of supplying an alternating signal of ultrasonic frequency and predetermined current and voltage to an electrode 13 connected to the metal implant and an electrode 14 (e.g., the housing of the device) in contact with the skin in proximity to the implant. The oscillator circuit 20 of the generator 12, shown in FIG. 3, is enclosed within the housing of the generator and is powered by a small 1.5 volt hearing aid battery 21 which delivers an output current in the range of 10 to 30 microamperes at 60 KHz to the electrodes 13 and 14 through an output resistor 22 which is selected or adjusted to yield the selected current within the specified range. The generator can be placed conveniently, e.g., in a missing molar space or cemented to a molar in the back of the mouth without disturbing the wearer of the device.

The signal applied to the electrodes is an alternating signal of symmetrical wave form and of substantially constant amplitude having a frequency in the range of from about 40 to 100 KHz and providing a constant alternating current in the range of from about 10 to 100 microamperes rms. In accelerating osseointegration of dental implants a constant current of 20 microamperes rms at 60 KHz is preferred.

The electrode 13 applied directly to the metal implant can be anchored thereto by any suitable means, such as a titanium screw 17 threaded directly into the titanium implant 10. In this way the patient can readily connect and disconnect the electrode 13 for intermittent use. The treatment should be continued long enough for the osseointegration of the implant to the stage at which a prosthetic or denture device can be mounted on the implant.

A verification study has been carried out by placing titanium implants in the tibia of rats using an electrical stimulator providing alternating current of 20 microamperes rms at a frequency of 60 KHZ with the results to date indicating that increased bone healing around the titanium metal implant can be increased substantially more than 50% by the electrical stimulation described above.

The present invention thus provides a method for the application of electrostimulation to the implant area which will increase the rate of osseointegration of the metallic implants in bone, thus increasing the speed and efficacy of healing. This, in turn, will reduce the interval between the surgical procedures in placing the implant into the bone and the mounting of a prosthetic or dental device on the implant and reduce the patient discomfort and costs associated with prolonged medical attention. The preliminary experiments conducted on rats have shown great promise and would lead to the conclusion that the same beneficial results could be achieved in human implants.

While a stimulating current of sinusoidal wave form was used in the experiments described above, it is believed that any alternating current wave form that is symmetrical about the axis, e.g., square and triangular wave forms, can be used.

The invention has been shown and described in preferred forms and by way of example, and modifications can be made therein within the spirit of the invention. The invention therefore is not intended to be limited to any specified form or embodiment except insofar as such limitations are expressly set forth in the claims.

I claim:

1. A method for accelerating osseointegration of a metal bone implant to anchor it in bone of a mammal comprising the steps of connecting at least one electrode with the implant and the other electrode with the skin in proximity to the implant, supplying to said electrodes an alternating electric signal of symmetrical wave form and of substantially constant amplitude having a frequency in the range of from about 40 to 100 KHz and providing a constant effective current in the range of from 10 to 100 microamperes rms and continuing the application of the signal to said electrodes for periods of time sufficient to accelerate the osseointegration.

2. A method as set forth in claim 1 in which the electrical signal has a frequency of about 60 KHz.

3. A method as set forth in claim 1 in which the electrical signal produces a constant current in the order of about 20 microamperes rms.

4. A method as set forth in claim 1 in which one of the electrodes is secured to the metal bone implant by an insertable and removable threaded titanium screw.

5. A method as set forth in claim 1 in which the metal implant is placed in a jawbone for the purpose of mounting a denture thereon.

6. A method as set forth in claim 5 in which one of the electrodes is free to float in the mouth to make contact with the gum.

7. A method as set forth in claim 1 wherein the two electrodes are supplied with an electrical signal of symmetrical wave form and of substantially constant amplitude at a frequency in the order of about 60 KHz and a constant effective current of about 20 microamperes rms.

8. A method as set forth in claim 7 in which the electrical signal is supplied by a miniature generator for placement within the mouth, the housing thereof serving as the other electrode for contact with the gum within the mouth.

9. A method as set forth in claim 5 in which the floating electrode is the housing of a generator supplying the electrical signal to the electrodes.

10. A method for accelerating osseointegration of a metal bone implant in a jawbone comprising the steps of connecting an electrode with the implant and another electrode being in contact with the gum within the mouth, supplying to said electrodes an alternating electrical signal of symmetrical wave form and substantially constant amplitude having a frequency in the range of from about 40 to 100 KHz and a constant effective current in the range of from 10 to 100 microamperes rms and continuing the application of the signal for periods of time sufficient to accelerate osseointegration.

11. A method as set forth in claim 10 in which the signal is supplied from a miniature generator sized for accommodation in the mouth.

* * * * *